United States Patent [19]
Wong

[11] Patent Number: 4,485,086
[45] Date of Patent: Nov. 27, 1984

[54] RADIOLABELED TUMOR IMAGING AGENT AND METHOD OF PREPARATION

[76] Inventor: Dennis W. Wong, 2853 Sunnydlen Rd., Torrance, Calif. 90505

[21] Appl. No.: 483,819

[22] Filed: Apr. 11, 1983

[51] Int. Cl.$^3$ .................... A61K 43/00; A61K 49/00
[52] U.S. Cl. .................... 424/1.1; 128/659; 206/569; 424/9
[58] Field of Search .............. 424/1.1, 9; 128/659; 206/569

[56] References Cited

U.S. PATENT DOCUMENTS 3,961,038 6/1976 Benes ........................... 424/1.1
4,421,735 12/1983 Haber et al. ................... 424/1.1

OTHER PUBLICATIONS

Cloutour et al., Int. J. Appl. Rad. Isot., 33, (1982), pp. 1311–1318.
Robinson et al., J. Nucl. Med., 23, (1982), p. P38.
Vaum et al., J. Pharmaceutical Sciences, 71, (1982), pp. 1223–1226.

Primary Examiner—Christine M. Nucker

[57] ABSTRACT

A novel chemical method of labeling porphyrin compounds, specifically hematoporphyrin derivative (HPD), with the radionuclide $^{111}$In or $^{113m}$In producing a radioactive tracer material suitable for biomedical applications. HPD labeled with $^{111}$In or $^{113m}$In is biologically active in vivo and is preferentially taken up by tumors. This provides a simple and specific means of localizing and detecting neoplasms in man or in animal by scintigraphic imaging techniques.

32 Claims, No Drawings

RADIOLABELED TUMOR IMAGING AGENT AND METHOD OF PREPARATION

BACKGROUND OF THE INVENTION

Clinical experience of the past decades has consistantly demonstrated that early tumor detection offers the best means of reducing high morbidity and mortality rates of cancer patients. Present clinical means of detecting neoplasms even with recent mdeical advances remains in many incidences a gross anatomical procedures relying upon various physical findings and radiographic diagnostic techniques to select a site for histologic sampling. Advances in radiography and the introduction of sonagraphy, xeroxgraphy and thermography have contributed significant improvement in detecting a large numbers of tumors. However, all these diagnostic means have inherent drawbacks and limitations, namely, a lack of sensitivity, specificity and reliability. Radiopharmaceuticals such as $^{111}$In-labeled bleomycin and $^{67}$Ga-gallium citrate are useful tumor imaging agents, but they lack specificity and sensitivity. Both agents are concentrated in inflammatory tissues and infectious lesions in addition to neoplasms.

Attempts to "mark" or "tag" cancer cells in order to differentiate them from normal tissue has been extensively investigated. Various fluorescent compounds such as tetracycline derivatives, acridine dyes and porphyrin compounds have been tried with mixed results. Of these, porphyrin compounds have shown remarkable affinity for neoplastic tissues.

Porphyrins and related analogs are complex tetrapyrrole compounds normally found in plants and in animals. They perform many vital biological functions by combining with metallic ions such as iron, magnesium, manganese, zinc, etc, . . . to form metalloporphyrins. Metalloporphyrins are essential for the normal metabolism of plant and animal. Many of these compounds exhibit strong fluorescence when exposed to an appropriate exciting light source.

Hematoporphyrin, an artifical porphyrin, is prepared by treating hemoglobin with concentrated sulfuric acid. It is a crude mixture of several porphyrins. Hematoporphyrin derivative(HPD), a recrystallized form of hematoporphyrin, is a complex mixture of hematoporphyrin diacetate, hematoporphyrin monoacetate, vinyl porphyrin, protoporphyrin, deuteroporphyrin and several addition analogs. The principle component in HPD is hematoporphyrin diacetate.(Lipson, R L, et al, J. Natl. Cancer Inst. 26: 1–11, 1961 and Clezy P. S., et al, Aust. J. Chem. 33: 585, 1980).

The preferential affinity of porphyrin compounds for various type of neoplasms has been known for more than four decades. When injected intravenously into tumor-bearing animal, a brilliant red-orange fluorescence is produced by ultra violet(UV) light activation of the porphyrin accumulated in the tumor. Hematoporphyrin derivative possesses higher tumor affinity than any other porphyrin compounds investigated. Successful clinical applications of HPD with human subjects in tumor detection have been documented in the literature (Sanderson, D R, et al, Cancer 30: 1368, 1972 and Kinsey, J H, et al. Mayo Clin. Proc. 53: 495, 1978).

Despite the initial optimism over possible diagnostic application of HPD in tumor detection, the usefulness of this agent is limited. This is primarily due to the fact that the HPD-fluorescence method involves invasive procedures. The fluorescence emitted by HPD must be activated in situ by a strong UV light source which requires highly sophisticated endoscopic fiberoptic equipments. Visual observation of the tissue fluorescence at best is subjective and varies widely from different investigators. Quenching of the fluorescence by normal tissue, body fluids and blood is a major obstacle in achieving significant reliability and reproducibility of this technique. Endoscopic procedures often produce tissue damages which lead to hemmorhage and subsequent masking of the tumor. Another major problem encountered is the inability to document photographically the fluorescence observed endoscopically. Complete reliance has to be placed on the visual interpretation and judgement of the endoscopist.

The use of radiolabeled HPD will eliminate most of the major problems encountered by the fluorescence-endoscopic procedures. Nuclear medicine techniques employing radiopharmaceuticals are simple and non-invasive. Following parenteral administration of the radiolabeled HPD, the radioactivity which concentrated in the tumor can be detected and documented on x-ray film by scintigraphic imaging means.

Several porphyrin compounds had been labeled with radionuclides such as $^{64}$Cu and $^{57}$Co. These radiolabeled porphyrins failed to achieve tumor localization in animal and human tumors (Wang T S T, et al, in Radiopharmaceuticals, Structure-Activity Relationship, Edited by R. P. Spencer, Grune and Stratton Press, New York 1981, pages 225–249). Earlier failures to localize neoplasms with radiolabeled porphyrins were attributed to: (1) poor labeling methodology; (2) alteration in biochemical property due to the labeling process; (3) a change in biochemical behavior of the parent porphyrin compound by the incorporation of the metallic ions; (4) in vivo instability of the labeled porphyrins; (5) the radionuclides used in the labeling process were incompatible with conventional scintigraphic imaging equipments.

At present, there are only two radionuclides of indium useful for medical applications. These are $^{111}$In and $^{113m}$In. Of these, $^{111}$In possess the most ideal radioisotopic characteristics for scintigraphic imaging procedures. It is a pure gamma emitter with a physical half-life of 2.83 days. Its gamma energy of 173 keV and 247 keV photons are compatible with conventional imaging equipments. Because of its longer half-life, $^{111}$In-based radiopharmaceuticals are ideally suited for imaging studies that require observation period in days or weeks. Optimal delayed images can be obtained with a single injection of a small dose of the radiolabeled compound and yet produces the minimal amount of radiation health hazard to the patient.

Indium-113m is also a pure gamma emitter. It emits a monoenergetic gamma photon of 393 keV which is compatible with existing scintillation Anger cameras. It has a relatively short physical half-life of 1.65 hours. Indium-113m based radiopharmaceuticals are not suitable for imaging studies that require observation period of more than 6 hours.

The common method of labeling porphyrins with radionuclides involves the reflux reaction of a porphyrin with a radioactive metallic salt in an acidic or basic medium. Dilute hydrochloric acid(HCl), acetic acid or dilute base such as sodium hydroxide (NaOH) is used to dissolve the porphyrin and to act as the reaction medium. An aqueous solution of cobaltous chloride ($^{57}$CoCl$_2$), cuprous chloride ($^{64}$CuCl$_2$) or $^{64}$Cu-acetate is added to the porphyrin solution and reflux for 30 minutes to up to 24–48 hours depending on the reactivity of the porphyrin used in the labeling process. The pH of the radioactive admixture is then adjusted to 6–8 whenever possible without causing denaturation or precipitation of the radiolabeled porphyrin. In many incidences, the labeled product must remain in either acidic or basic condition in order to insure chemical and labeling stability.

Although the labeling process is quite simple, but the labeling yield is unsatisfactory, ranging from 10–40%. The final labeled product contains many radioactive impurities. These include free or unbound radionuclide, denatured by products and insoluble radiocolloids in the form of hydroxide such as $^{57}Co(OH)_2$ or $^{64}Cu(OH)_2$. Without extensive purification processes, these preparations are not useful or suitable for medical applications.

The present invention, that is, a chemical method of labeling porphyrins or hematoporphyrin derivative(HPD) with the radionuclides of indium, offers many advantages over earlier techniques. These include: (1) the labeling process can proceed in aqueous medium at neutral pH 7–8 condition without the problems of denaturation or decomposition; (2) the radionuclide is firmly bound to the porphyrin ligand; (3) the labeling yield is greater than 98% with consistant reproducibility and reliability; (4) the radiolabeled porphyrin is stable in vitro and in vivo as confirmed by radiochemical and anamal assays; (5) the labeled product is clear and freed from microcolloids contamination and can be given to patient by parenteral routes; (6) unlike other radiolabeled porphyrins, $^{111}$In- or $^{113m}$In-labeled porphyrin is preferentially accumulated by neoplasms; (7) because of long half-life of $^{111}$In, the condition of the patient can be followed for days with a single injection of $^{111}$In-labeled porphyrin compound.

SUMMARY OF THE INVENTION

The present invention relates to the development of a radiolabeled porphyrin compound useful for biomedical applications. Specifically, it is a novel chemical method of labeling a porphyrin compound such as hematoporphyrin derivative (HPD) with the radionuclides of indium, $^{111}$In or $^{113m}$In, producing a diagnostic agent suitable for radiologic imaging of neoplasms. In the labeling process, $^{111}$InCl$_3$ or $^{113m}$InCl$_3$ is first converted to radioactive In bicarbonate, In citrate or In acetate by reacting InCl$_3$ with a solution of sodium bicarbonate(-NaHCO$_3$), sodium citrate or sodium acetate. The pH of the radioactive mixture is then adjusted to 7.4 with 0.1N NaOH when needed. An aqueous solution of porphyrin or HPD is brought in contact with the neutralized In bicarbonate, In citrate or In acetate. After reflux at 110°–120° C. for 15 minutes, the radionuclide is firmly bound to the porphyrin ligand forming a stable $^{111}$In- or $^{113m}$In-labeled porphyrin or HPD suitable for parenteral injection without further purification. Following intravenous injection, the radiolabeled HPD or porphyrin is rapidly taken by tumors with increased radioactivity accumulating at these sites. This provides a simple and rapid means of localizing and detecting the presence of neoplasms in man or in animal by scintigraphic imaging procedures. Based on the present chemical process, a non-radioactive labeling reagent kit with long shelve-life can be prepared in advance to facilitate the in-house preparation of $^{111}$In- or $^{113m}$In-labeled porphyrin or HPD.

DETAILED DESCRIPTION OF THE INVENTION

This invention relates to the development of a novel radiopharmaceutical useful for the localization and detection of neoplasma. Specifically, it relates to a chemical method of labeling porphyrin or hematoporphyrin derivative(HPD) with the radionuclide of indium producing a radiolabeled substance suitable for biomedical applications. The invention further relates to a prepackaged non-radioactive labeling reagent kit based on the said labeling process and a simple method of using said labeling reagent kit for producing $^{111}$In- or $^{113m}$In-HPD injection with generally available $^{111}$InCl$_3$ or $^{113m}$InCl$_3$ solution.

The basic methodology of the present invention for labeling a porphyrin compound with the radionuclides of indium, $^{111}$In or $^{113m}$In, consists of the following sequential chemical reactions: (1) initial conversion of the radioactive indium trichloride($^{111}$InCl$_3$ or $^{113m}$InCl$_3$) to indium bicarbonate, indium citrate or indium acetate by reacting InCl$_3$ with sodium bicarbonate, sodium citrate or sodium acetate; (2) adjust the pH of the reaction medium to 7.4 and 0.1N NaOH solution when needed; (3) binding of the indium radionuclide to the porphyrin ligand by adding an aqueous solution of porphyrin to the neutralized reaction mixture and heating the admixture at 110°–120° C. for 15 minutes; (4) allow the final labeled product to cool to room temperature for 10–30 minutes.

The source of indium radionuclides should be water-soluble with the preferred source being radioactive indium bicarbonate, indium citrate or indium acetate solution. However, these prepartions are not commercially available at present but can be prepared by reacting indium trichloride solution with sodium bicarbonate, sodium citrate or sodium acetate. Indium-111 is available as $^{111}$InCl$_3$ dissolved in 0.05N HCl. $^{113m}$In can be obtained by eluting a $^{113}$Sn-$^{113m}$In generator with 0.05N HCl. Bother preparations are acidic with a pH of less than 3.

Both $^{111}$InCl$_3$ and $^{113m}$InCl$_3$ are stable only in acidic medium. Increasing the pH of the medium above 3 with dilute alkali such as 0.1N NaOH will convert the trichloride salt into insoluble indium hydroxide colloid. In accordance with the labeling methodology of the present invention, $^{111}$InCl$_3$ or $^{113m}$InCl$_3$ must be converted to other soluble indium salts such as bicarbonate, citrate or acetate that are chemically active and stable at neutral pH condition. This is accomplished by reacting $^{111}$InCl$_3$ or $^{113m}$InCl$_3$ with a solution of sodium bicarbonate, sodium citrate or sodium acetate. The pH of the radioactive mixture is then adjusted to 6–8, preferably 7.4, prior to labeling with a porphyrin compound.

In order to prevent insoluble hydroxide formation, it is extremely important that sodium salt should react with $^{111}$InCl$_3$ or $^{113m}$InCl$_3$ first before pH adjustment. With NaHCO$_3$, pH adjustment with 0.1N NaOH is unnecessary. Addition of a small amount, less than 1 ml, of NaHCO$_3$ solution is adequate to convert radioactive InCl$_3$ to In-bicarbonate and at the same time increases the pH of the reaction medium to 7.4. Depending on the amount of InCl$_3$ solution initially used in this reaction, the amount of NaHCO$_3$ solution required to complete the reaction at neutral pH can be determined by simple experiment by those who are skilled in the art.

Unlike NaHCO$_3$, a large amount in excess of 10 ml of either sodium citrate or sodium acetate solution is needed to neutralize the reaction medium to pH 7.4. This is highly undesirable because such a large volume for pH adjustment will dilute the final concentration of the labeled product. A better formulation would be to use a small amount, usually 1-2 ml, of either sodium citrate or sodium acetate to convert the $InCl_3$ to the corresponding indium salt. The pH of the reaction medium is then adjusted to 7.4 with 0.1N NaOH solution prior to the addition of a porphyrin solution. The amount of 0.1N NaOH solution needed for pH adjustment can be determined by simple routine experiment by those who are skilled in the art.

Solution of $NaHCO_3$, sodium citrate or sodium acetate are stable at room temperature or at 20°-8° C. for up to 2 years when properly prepared and stored. Preferably, these reagents are prepared and packaged in the form of a freeze-dried solid which aids in shipping and storage. The lyophilized solid must be reconstituted with distilled water at time of use.

Because of a favorable long half-life, solution of $^{111}In$ bicarbonate, citrate or acetate can be prepared in advance and stored as such following the reaction of $^{111}InCl_3$ with $NaHCO_3$, sodium citrate or sodium acetate. Alternatively, the pH of these solution can be adjusted to 7.4 with 0.1N NaOH so desired and stored under proper condition. Preferably, these solutions are prepared and stored in the form of a freeze-dried solid. The lyophilized radioactive solid can be reconstituted with distilled water to a desired concentration at time of use.

The present invention can label any porphyrin compounds with the radionuclides of indium. A variety of these substances are commercially available in relatively pure form. These include coproporphyrins, protoporphyrins, uroporphyrins, deuteroporphyrins, vinyl porphyrin, hematoporphyrin and its salt hematoporphyrin dihydrochloride, hematoporphyrin derivative, tetraphenylporphime sulfonate and other related analogs. It is essential that these porphyrin compounds are dissolved in aqueous media such as normal saline, distilled water or suitable buffers having a pH above 7. HPD is preferred in the present invention, since it has been known to be a better tumor marker than any porphyrin compounds investigated.

Hematoporphyrin derivative(HPD) is prepared by the method of Lipson(Lipson, R L, et al: J. Natl. Cancer Inst. 26: 1,1961) and redissolved in pH 7.4 normal saline. The neutral HPD solution is sterilized by ultrafiltration technique and packaged in dark amber-colored ampoule or serum vial in a concentration of 5-10 mg/ml. It is essential that the pH of the HPD solution be maintained above 7 to avoid reprecipitation. HPD is unstable in acidic medium. Below pH 7, it will be precipitated out from solution. Lyophilization of this reagent is unnecessary since HPD solution is stable indefinitely at room temperature or at 2°-8° C. Any pharmacologically acceptable buffers having a pH above 7 such as bicarbonate, citrate, acetate or phosphate buffer systems can be used to stabilize the HPD solution.

The amount of HPD that can be labeled with the radionuclides of indium varies from 0.1 mg to 1000 grams. In the present invention, 0.5-10 ml containing 5-100 mg of HPD is sufficient to bind up to 1000 mCi of $^{111}In$ or $^{113m}In$.

EXAMPLE 1

Procedure for labeling hematoporphyrin derivative with $^{111}In$ or $^{113m}In$ using the sodium bicarbonate reaction 1. To a sterile serum vial containing 5 ml (10 mCi) $^{111}InCl_3$ or $^{113m}InCl_3$ solution, add sufficient amount of 7.5% $NaHCO_3$ solution to raise the pH of the $InCl_3$ solution to 7.4.
2. Add 0.5-1 ml HPD solution providing 5-10 mg of HPD to the neutralized indium solution and mix gently for 1-5 minutes.
3. Heat the contents of the reaction vial at 110°-120° C. for 15 minutes.
4. Allow the contents of the reaction vial to cool to room temperature for 10-30 minutes.
5. Perform qualitative and quantitative radiochemical assays.
6. For scintigraphic imaging, a dose of 50 uCi to 2 mCi $^{111}In$-HPD or $^{113m}In$-HPD is sufficient to detect various types of tumors by scanning the patient with a scintillation Anger camera and by observing areas of increased radioactivity at the sites of these lesions as seen in the scan.

EXAMPLE 2

Procedure for labeling HPD with $^{111}In$ or $^{113m}In$ using sodium citrate or sodium acetate reactions 1. To a sterile serum vial containing 5 ml (10 mCi) $^{111}InCl_3$ or $^{113m}InCl_3$ solution, add 1-2 ml sodium citrate(5%) or sodium acetate(5%) solution and mix gently for 1-5 minutes.
2. Raise the pH of the contents of the reaction vial to 7.4 with sufficient amount of 0.1N NaOH solution.
3. Add 0.5-1 ml HPD solution providing 5-10 mg of HPD to the neutralized indium solution and mix gently for 1-5 minutes.
4. Heat the contents of the reaction vial at 110°-120° C. for 15 minutes.
5. Allow the contents of the reaction vial to cool to room temperature for 10-30 minutes.
6. Perform qualitative and quantitative radiochemical assays.

The above procedures as described in Examples 1 and 2 are not limited for preparing small amount of radiolabeled HPD. A higher concentration in excess of 10 to 100 Curies(Ci) of $^{111}In$-HPD can be prepared by minor adjustment in the formulation. The amount of the reagents required to produce high activity radiolabeled HPD can be determined by simple routine experiment by those who are skilled in the art. These procedures can be used to label other porphyrin compounds or their derivatives.

Based on the chemical labeling process as described above, an instant non-radioactive labeling reagent kit can be prepared in advance with individual components packaged separately in sealed, sterile, apyrogenic containers. Such a labeling reagent kit will facilitate the in-house preparation of radiolabeled porphyrin or HPD injection at individual nuclear medicine facility whenever so desired. The labeling reagent kit is specially useful for preparing short half-life $^{113m}In$-labeled porphyrin or HPD. Because of a short half-life of 1.65 hour, $^{113m}In$-based radiopharmaceuticals must be prepared in-house at user's site. The labeling reagent kit is comprised of three basic reagents: (1) a sterile aqueous solution of sodium bicarbonate, sodium citrate or sodium acetate; (2) a dilute alkaline solution for pH adjustment. (This reagent is not required for labeling procedure based on the sodium bicarbonate reaction) and (3) an aqueous solution of porphyrin or HPD in a concentration of 5-10 mg/ml dissolved in pH 7.4 normal saline or distilled water.

EXAMPLE 3

Formulation of non-radioactive labeling reagent kit for preparing $^{111}$In- or $^{113m}$In-labeled HPD injection

Labeling reagent kit A

The following reagents are essential for preparing radiolabeled HPD based on the sodium bicarbonate reaction.

Vial #1. Sodium bicarbonate reagent.

Each vial contains 2-5 ml of an aqueous solution of 7.5% sodium bicarbonate. This reagent can be packaged in liquid form or in the form of a freeze-dried solid. The latter must be reconstituted with same volume of Water for Injection at time of use.

Vial #2. Aqueous porphyrin or HPD solution.

Each dark amber-colored vial contains 5-10 mg of a porphyrin compound or HPD dissolved in 1 ml pH 7.4 normal saline. This reagent should not be lyophilized but should be stored in liquid form either at room temperature or at 2°-8° C.

Labeling reagent kit B

This reagent kit is based on the conversion of radioactive indium trichloride to indium citrate or indium acetate reaction.

Vial #1. Sodium citrate or sodium acetate reagent.

Each vial contains 2-5 ml of an aqueous solution of either 5% Na citrate or sodium acetate. This reagent can be packaged either in liquid form or in the form of a freeze-dried solid. The latter must be reconstituted with same volume of Water for Injection at time of use.

Vial #2. Dilute alkaline solution.

Each vial contains 1-5 ml of an aqueous solution of 0.1N NaOH. This reagent can be packaged either in liquid form or in the form of a freeze-dried solid. The latter must be reconstituted with the same volume of Water for Injection at time of use.

Vial #3. Aqueous porphyrin or HPD solution.

Each dark amber-colored vial contains 5-10 mg of a porphyrin compound or HPD dissolved in 1 ml pH 7.4 normal saline. This reagent should not be lyophilized but should be stored in liquid form either at room temperature or at 2°-8° C.

In use, the active ingredients of said labeling reagent kit are mixed with a source of radioactive indium trichloride solution and then heated at 110°-120° C. for 15 minutes in order to form an efficiently labeled radioactive porphyrin compound or HPD suitable for scintigraphic imaging of tumors. The following examples illustrate the labeling procedures for preparing $^{111}$In- or $^{113m}$In-HPD injection:

EXAMPLE 4

Procedure for preparing $^{111}$In-HPD or $^{113m}$In-HPD injection utilizing the labeling reagent kit A of Example 3 based on the sodium bicarbonate reaction The direction outlined below must be carefully followed for optimum preparation of radiolabeled HPD injection.

1. Remove the labeling reagent kit from the refrigerator and warm to room temperature before continuing.
2. Reconstitute the lyophilized sodium bicarbonate reagent with 2-5 ml Water for Injection until completely dissolved.
3. To a sterile vial containing 0.5-5 ml(1-10 mCi) $^{111}$InCl$_3$ or $^{113m}$InCl$_3$ solution, inject sufficient amount of the reconstituted NaHCO$_3$ solution to raise the pH of the radioactive indium trichloride solution to 7.4. Check the pH with litmus paper before continuing.
4. Shake the contents of the reaction vial gently for 1-2 minutes.
5. Inject 1 ml (5-10 mg) of the HPD solution into the reaction vial slowly with gentle swirling.
6. Heat the contents of the reaction vial at 110°-120° C. for 15 minutes.
7. Allow the contents of the reaction vial to cool to room temperature for 10-30 minutes.
8. Do not use the preparation after 3 months from the time of preparation if kept at room temperature or 6 months if kept at 2°-8° C.

EXAMPLE 5

Procedure for preparing $^{111}$In-HPD or $^{113m}$In-HPD injection utilizing the labeling reagent kit B based on the sodium citrate or sodium acetate reaction 1. Remove the labeling reagent kit from the refrigerator and warm to room temperature before continuing.
2. Reconstitute the lyophilized sodium citrate or sodium acetate reagent with 2-5 ml Water for Injection until completely dissolved.
3. Reconstitute the lyophilized dilute alkaline reagent with 1-5 ml Water for Injection until completely dissolved.
4. To a sterile vial containing 0.5-5 ml(1-10 mCi) $^{111}$InCl$_3$ or $^{113m}$InCl$_3$ solution, inject 1 ml of the reconstituted sodium citrate or sodium acetate solution and mix for 1-2 minutes.
5. Raise the pH of the radioactive indium solution of Step (4) to 7.4 with a sufficient amount of the reconstituted 0.1N NaOH solution. Check the pH with litmus paper before continuing.
6. Shake the contents of the reaction vial gently for 1-2 minutes.
7. Inject 1 ml (5-10 mg) of the HPD solution into the reaction vial slowly with gentle swirling.
8. Heat the contents of the reaction vial at 110°-120° C. for 15 minutes.
9. Allow the contents of the reaction vial to cool to room temperature for 10-30 minutes.
10. Do not use the preparation after 3 months from the time of preparation if it is kept at room temperature or 6 months if it is kept at 2°-8° C.

The binding efficiency or labeling yield of $^{111}$In-HPD or $^{113m}$In-HPD can be determined by ascending paper radiochromatography with Whatman No. 1 paper or thin layer radiochromatography with silica gel plates (ITCL-SG) developed in 0.1N HCl. Free or unbound radionuclide will migrate toward the solvent front with a Rf value of 1.0, whereas, $^{111}$In-HPD or $^{113m}$In-HPD will remain at the origin of the radiochromatogram (Rf=0.0). Additionally, the radiolabeled HPD can be assessed by acid precipitation method with 0.1N HCl. At isoelectric point of pH 3.5, the radiolabeled HPD will be precipitated out from solution as insoluble crystals, whereas, free or unbound radionuclide will remain in the supernatant following centrifugation and separation processes.

Data from radiochemical analyses indicate that of a total of 10 batches of HPD labeled with $^{111}$In, an average binding efficiency of greater than 98% was achieved with less then 2% free or unbound radionuclide. Acid precipitation analyses confirmed that the radionuclide $^{111}$In was firmly bound to HPD ligand. Greater than 98% of the $^{111}$In radioactivity was found to be associated with the acid precipitate. These data also suggested that all the components in the HPD solution were labeled with $^{111}$In. Although not wish to be bound by theory, labeling of HPD with $^{111}$In appearred to involve the incorporation of the radionuclide into the tetrapyrrole ring forming a stable radiometalloporphyrin chelate. Similar to unlabeled HPD, $^{111}$In-HPD exhibited brilliant fluorescence when activated with a ultra violet light source.

The efficacy of $^{111}$In-HPD to localize and to detect tumors was investigated with two animal models. Spontaneous mammary adenocarcinomas developed from outbred CFW strain Swiss-Webster female white mice and chemical carcinogen (7,12-DMBA) induced breast tumors in female Sprague-Dawley white rats were selected for tumor imaging studies. Following intraperitoneal or intravenous injection (50 uCi/mouse or 300 uCi/rat), whole body anterior scans or images were obtained at various time intervals, e.g. from 0.5 to 24 hours and at 48 and 72 hours, with an Anger scintillation camera. Increased radioactivity at the sites of these lesions indicated the presence of tumors. After imaging, the animals were sacrificed. Various vital organs, blood and tumors were collected, weighted and assessed for radioactivity. Microscopic tissue slides from tissue samples were obtained for histologic identification of the tumors.

Imaging results confirmed that $^{111}$In-labeled HPD localized in malignant and benign breast tumors. With the exception of large necrotic tumors, all viable tumors were well delineated in the scintigrams. Scintigraphic images obtained after a 24 to 48 hours delay produced the best imaging results and confirmed by tissue distribution data. Autopsy findings confirmed the locations of these tumors corresponding to the areas of increased radioactivity found in the scintigrams. Histologic inspection showed that these tumors were mammary adenocarcinomas of ductal origin. There was considerable necrosis with liquefaction of the central portion of the tumors, sometimes leading to rupture and secondary infection.

The mechanism of tumor uptake of HPD is not known. Tissue distribution studies confirmed that $^{111}$In-labeled HPD was indeed preferentially taken by animal tumors. With the exception of the liver, spleen and the kidneys, highest concentration of $^{111}$In-HPD was found in the neoplasma. The new radiopharmaceutical appeared to be metabolized in the liver and eliminated by the kidneys.

The above examples and the described procedures are for illustrative purposes only and are not intended to be limiting of the scope of the invention. It will be apparent to those skilled in the art that both may be modified within the scope of the invention defined in the following claims.

I claim:

1. A method of labeling porphyrin compounds, analogs, derivatives and substances containing porphyrin with the radionuclide of indium at physiologic pH 7-8 condition which comprises the sequential steps of:
   (a) reacting an acidic solution of radioactive trichloride of indium with a water soluble sodium salt;
   (b) raising the pH of the admixture of step (a) to 7.4 with a solution of dilute alkali;
   (c) adding to the neutralized solution of step (b) 0.5-10 ml of an aqueous solution of a porphyrin compound desired to be labeled;
   (d) heating the admixture of step (c) at 110°-120° C. for 15 minutes and allowing it to cool to room temperature for 10-30 minutes.

2. A method according to claim 1, wherein said radionuclide of indium is selected from the group consisting $^{111}$In and $^{113m}$In.

3. A method according to claim 2, wherein said radionuclide of indium is an aqueous solution of $^{111}$InCl$_3$ or $^{113m}$InCl$_3$ providing from 0.1 mCi-10,000 mCi of radioactivity.

4. A method according to claim 1, wherein said sodium salt is selected from the group consisting sodium bicarbonate, sodium citrate and sodium acetate.

5. A method according to claim 4, wherein said sodium salt is an aqueous solution of 1-10% sodium bicarbonate, sodium citrate or sodium acetate.

6. A method according to claim 5, wherein said sodium salt solution is an aqueous solution of 7.5% sodium bicarbonate, 5% sodium citrate or 5% sodium acetate.

7. A method according to claim 1, wherein said dilute alkali is an aqueous solution of 0.01N to 1N sodium hydroxide(NaOH).

8. A method according to claim 7, wherein said dilute alkali is an aqueous solution of 0.05N to 0.1N NaOH having a pH of above 12.

9. A method according to claim 1, wherein said porphyrin compound is selected from the group consisting uroporphyrin, protoporphyrin, deuteroporphyrin, coproporphyrin, vinyl porphyrin, hematoporphyrin, hematoporphyrin dihydrochloride, tetraphenylporphine sulfonate and hematoporphyrin derivative(HPD).

10. A method according to claim 9, wherein said porphyrin compound is dissolved in an aqueous medium having a pH of above 7.

11. A method according to claim 10, wherein said porphyrin compound is present in the amount of 0.1-1000 mg dissolved in distilled water or normal saline adjusted to a pH of 7-8 with 0.1N to 1N NaOH.

12. A method according to claim 11, wherein said porphyrin compound is present in the amount of 5-100 mg dissolved in pH 7.4 normal saline together with any pharmaceutically acceptable preservative or stabilizer.

13. A method of labeling hematoporphyrin derivative (HPD) with $^{111}$In at physiologic pH 7-8 condition based on the bicarbonate reaction with $^{111}$InCl$_3$ producing a diagnostic composition suitable for radiologic imaging of neoplasms in man or in animal comprising the sequential steps of:
   (a) converting $^{111}$InCl$_3$ to $^{111}$In-bicarbonate by neutralizing 0.5-5 ml(1-10 mCi) $^{111}$InCl$_3$ solution to pH 7.4 with a sufficient amount of a 7.5% sodium bicarbonate solution and mixing the admixture for 1-5 minutes;
   (b) adding 0.5-1 ml(5-10 mg) HPD solution to the neutralized radioactive solution of step (a) and mixing it for 1-5 minutes;
   (c) heating the radioactive admixture of step (b) at 110°-120° C. for 15 minutes and allowing it to cool to room temperature for 10-30 minutes.

14. A method of labeling HPD with $^{111}$In at physiologic pH 7-8 condition based on the citrate or acetate reaction with $^{111}$InCl$_3$ producing a diagnostic composition suitable for radiologic imaging of neoplasms in man or in animal comprising the sequential steps of:
   (a) reacting 0.5-5 ml(1-10 mCi)$^{111}$InCl$_3$ solution with 1-2 ml of an aqueous solution of either 5% sodium citrate or 5% sodium acetate to form the corresponding soluble indium salt and mixing the admixture for 1-5 minutes;
   (b) raising the pH of the admixture of step (a) to 7.4 with a sufficient amount of 0.1N NaOH solution;
   (c) adding 0.5-1 ml(5-10 mg) HPD solution to the neutralized radioactive solution of step (b) and mixing it for 1-5 minutes;
   (d) heating the radioactive admixture of step (c) at 110°-120° C. for 15 minutes and allowing it to cool to room temperature for 10-30 minutes.

15. Hematoporphyrin derivative(HPD), a compound selected from the group of porphyrins is labeled with $^{111}$In according to the method of claim 13 or claim 14.

16. A method of localizing and detecting neoplasms in mammal by scintigraphic imaging procedures comprising:
   (a) administering intravenously to said mammal 50 uCi to 5 mCi of $^{111}$In-HPD labeled according to the method of claim 13 or claim 14;
   (b) scanning said mammal with a conventional scintillation Anger camera or a rectilinear scanner at various time intervals from 0.5 hours to up to 2 weeks;
   (c) observing increasing radioactivity accumulated at the sites of these lesions as seen in the scintigrams.

17. A kit for labeling porphyrin compounds, analogs, derivatives and substances containing porphyrin with $^{111}$In or $^{113m}$In at physiologic pH 7-8 condition based on the bicarbonate reaction with $^{111}$InCl$_3$ or $^{113m}$InCl$_3$ comprising a sodium bicarbonate solution and an aqueous solution of a porphyrin compound aseptically prepared and packaged separately in sealed, sterile, apyrogenic containers wherein said kit is used with an aqueous solution of $^{111}$InCl$_3$ or $^{113m}$InCl$_3$.

18. A kit according to claim 17, wherein said sodium bicarbonate solution is an aqueous solution of 7.5% sodium bicarbonate dissolved in distilled water.

19. A kit according to claim 18, wherein 1-5 ml of an aqueous solution of 7.5% NaHCO$_3$ is packaged in the form of a freeze-dried solid as said sodium bicarbonate solution.

20. A kit according to claim 17, wherein said porphyrin compound is selected from the group consisting uroporphyrin, protoporphyrin, deuteroporphyrin, coproporphyrin, vinyl poprhyrin, hematoporphyrin, hematoporphyrin dihydrochloride, tetraphenylporphine sulfonate and hematoporphyrin derivative(HPD).

21. A kit according to claim 20, wherein said porphyrin compound is HPD dissolved in an aqueous medium in the concentration of 1-100 mg/ml having a pH of 7-8.

22. A kit according to claim 21, wherein said HPD is present in the amount of 5-10 mg dissolved in 1-2 ml pH 7.4 normal saline together with any pharmaceutically acceptable preservative or stabilizer.

23. A method of preparing $^{111}$In- or $^{113m}$In-labeled HPD injection at physiologic pH 7-8 condition based on the bicarbonate reaction with $^{111}$InCl$_3$ or $^{113m}$InCl$_3$ suitable for use in radiologic imaging of neoplasms in mammal which comprises the sequential steps of:
   (a) reconstituting the lyophilized sodium bicarbonate reagent with 1-5 ml Water for Injection until completely dissolved;
   (b) injecting 0.5-50 ml(1-100 mCi) of either $^{111}$InCl$_3$ or $^{113m}$InCl$_3$ solution into a sterile serum vial;
   (c) raising the pH of the radioactive indium trichloride solution to 7.4 with a sufficient amount of the reconstituted sodium bicarbonate solution and mixing the radioactive admixture for 1-5 minutes;
   (d) adding to the neutralized solution of step (c) 0.5-1 ml(5-10 mg) of the HPD solution slowly and mixing it for 1-5 minutes;
   (e) heating the contents of the reaction vial at 110°-120° C. for 15 minutes and allowing it to cool to room temperature for 10-30 minutes.

24. A kit for labeling porphyrin compounds, analogs, derivatives and substances containing porphyrin with $^{111}$In or $^{113m}$In at physiologic pH 7-8 condition based on the citrate or acetate reaction with $^{111}$InCl$_3$ or $^{113m}$InCl$_3$ comprising a sodium salt reagent, a dilute alkali and an aqueous solution of a porphyrin compound aseptically prepared and packaged separately in sealed, sterile, apyrogenic containers wherein said kit is used with an aqueous solution of $^{111}$InCl$_3$ or $^{113m}$InCl$_3$.

25. A kit according to claim 24, wherein said sodium salt reagent is an aqueous solution of either 5% sodium citrate or 5% sodium acetate.

26. A kit according to claim 25, wherein 1-5 ml of either sodium citrate or sodium acetate solution is packaged in the form of a freeze-dried solid as said sodium salt reagent.

27. A kit according to claim 24, wherein said dilute alkali is an aqueous solution of 0.1N NaOH.

28. A kit according to claim 27, wherein 1-5 ml of the 0.1N NaOH is packaged in the form of a freeze-dried solid as said dilute alkali.

29. A kit according to claim 24, wherein said porphyrin compound is selected from the group consisting uroporphyrin, protoporphyrin, deuteroporphyrin, coporphyrin, vinyl porphyrin, hematoporphyrin, hematoprophyrin dihydrochloride, tetraphenylporphine sulfonate and hematoporphyrin derivative(HPD).

30. A kit according to claim 29, wherein said porphyrin compound is HPD dissolved in an aqueous medium in a concentration of 1-100 mg/ml having a pH of 7-8.

31. A kit according to claim 30, wherein said HPD is present in the amount of 5-10 mg dissolved in 1-2 ml pH 7.4 normal saline together with any pharmaceutically acceptable preservative or stabilizer.

32. A method of preparing $^{111}$In- or $^{113m}$In-labeled HPD injection at physiologic pH 7-8 condition based on the citrate or acetate reaction with $^{111}$InCl$_3$ or $^{113m}$InCl$_3$ suitable for use in radiologic imaging of neoplasms in mammal which comprises the sequential steps of:
   (a) reconstituting the lyophilized sodium salt reagent-(sodium citrate or sodium acetate) with 1-5 ml Water for Injection until completely dissolved;
   (b) reconstituting the lyophilized dilute alkali with 1-5 ml Water for Injection until completely dissolved;
   (c) injecting 0.5-50 ml (1-100 mCi) of either $^{111}$InCl$_3$ or $^{113m}$InCl$_3$ solution into a sterile serum vial;
   (d) adding 1-2 ml of the sodium salt solution to the radioactive indium trichloride solution and mixing the admixture for 1-5 minutes;
   (e) raising the pH of the admixture of step (d) to 7.4 with a sufficient amount of 0.1N NaOH solution.
   (f) adding to the neutralized solution of step (e) 0.5-1 ml(5-10 mg) of the HPD solution slowly and mixing it for 1-5 minutes;
   (g) heating the contents of the reaction vial at 110°-120° C. for 15 minutes and allowing it to cool to room temperature for 10-30 minutes.

* * * * *